(12) United States Patent
Takenaka et al.

(10) Patent No.: US 10,548,755 B2
(45) Date of Patent: Feb. 4, 2020

(54) MOTION ASSIST DEVICE

(71) Applicant: HONDA MOTOR CO., LTD., Tokyo (JP)

(72) Inventors: Toru Takenaka, Wako (JP); Kei Shimada, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 332 days.

(21) Appl. No.: 15/790,459

(22) Filed: Oct. 23, 2017

(65) Prior Publication Data
US 2018/0125692 A1 May 10, 2018

(30) Foreign Application Priority Data
Nov. 4, 2016 (JP) .................................. 2016-216315

(51) Int. Cl.
*A61F 5/01* (2006.01)
*A61H 3/00* (2006.01)
*A61H 1/02* (2006.01)

(52) U.S. Cl.
CPC ......... *A61F 5/0102* (2013.01); *A61H 1/0237* (2013.01); *A61H 3/00* (2013.01); *A61H 1/024* (2013.01); *A61H 1/0244* (2013.01); *A61H 2201/1215* (2013.01); *A61H 2201/1223* (2013.01); *A61H 2201/1418* (2013.01); *A61H 2201/1436* (2013.01); *A61H 2201/165* (2013.01); *A61H 2201/1623* (2013.01); *A61H 2201/1628* (2013.01); *A61H 2201/1642* (2013.01); *A61H 2201/5007* (2013.01); *A61H 2201/5069* (2013.01)

(58) Field of Classification Search
CPC .. A61F 5/0102; A61F 5/0125; A61F 5/05841; A61F 5/05833; A61F 2005/0132; A61F 2005/0134; A61F 2005/0137; A61F 2005/0139; A61F 2005/0146; A61F 2005/016; A61F 2005/0183; A61H 1/02; A61H 1/0237; A61H 1/024; A61H 1/0244; A61H 1/0255; A61H 1/0218; A61H 1/0262; A61H 3/00; A61H 2201/1215; A61H 2201/1223; A61H 2201/1418; A61H 2201/1436; A61H 2201/1623; A61H 2201/1628; A61H 2201/1642; A61H 2201/165; A61H 2201/5007; A61H 2201/5069
USPC .......................................................... 601/5
See application file for complete search history.

(56) References Cited

U.S. PATENT DOCUMENTS

| 2015/0209215 A1 | 7/2015 | Lee et al. | |
|---|---|---|---|
| 2015/0335515 A1* | 11/2015 | Lee ........................ | A61H 3/008 601/5 |
| 2016/0038313 A1* | 2/2016 | Kim ......................... | F16H 7/02 623/24 |

(Continued)

FOREIGN PATENT DOCUMENTS

JP       2015136623 A     7/2015

*Primary Examiner* — Kendra D Carter
*Assistant Examiner* — Paige Kathleen Bugg
(74) *Attorney, Agent, or Firm* — Armstrong Teasdale LLP

(57) ABSTRACT

Provided is a motion assist device that can minimize the number of actuators that are required for assisting a certain mode of motion of the user while allowing a greater freedom of motion beside from the motion which the motion assist device is designed to assist. A power transmission mechanism for the device includes a belt drive mechanism which is incorporated with a differential mechanism.

11 Claims, 17 Drawing Sheets

(56) References Cited

U.S. PATENT DOCUMENTS

2016/0310344 A1* 10/2016 Shimada .................. A61H 3/00
2017/0319421 A1* 11/2017 Julin ........................ A61H 3/00
2017/0348176 A1* 12/2017 Herr ...................... B25J 9/0006
2017/0367919 A1* 12/2017 Vitiello ................ A61H 1/0244

* cited by examiner

MOTION ASSIST DEVICE

TECHNICAL FIELD

The present invention relates to a motion assist device for assisting a motion of a body part of a user such as hip joints and knee joints.

BACKGROUND ART

Various motion assist devices configured to be worn by a user have been proposed for clinical purposes and improved life quality. Motion assist devices are often designed as walking assist devices for assisting the walking motion of the user, and power boosting devices for aiding a worker to work under heavy burdens or to perform other strenuous forms of work.

The motion assist device disclosed in JP2015-136623A is configured to assist the motion of the legs of the user, and uses a cable for transmitting the power. This motion assist device includes a pelvic support member configured to be worn on the pelvic part of the user, a pair of first frames each having one end connected to a corresponding one of the lateral ends of the pelvic support member via a pivot joint so as to be rotatable around a laterally extending axial line and configured to be secured to an upper leg of the user, a pair of second frames connected to the other ends of the respective first frames each via a pivot joint so as to be rotatable around a laterally extending axial line and configured to be secured to the respective lower legs of the user, and actuators mounted on the pelvic support member. The power of the actuators are transmitted to the various pivot joints each via a pulley and cable power transmission mechanism.

According to this prior art, a same number of actuators as the number of the joints to be assisted are required. Furthermore, when the user performs a motion such as sitting and stooping which is not assisted by the device, the user encounters a considerable resistance caused by the actuators which are turned off. As the actuators typically consist of permanent magnet motors, even when the actuators are turned off, a considerable torque is required to overcome the resistance of the actuators. In particular, when a gear reduction mechanism is provided in each actuator, it may be impossible for the user to rotate or otherwise move the output end of the actuator.

SUMMARY OF THE INVENTION

In view of such a problem of the prior art, a primary object of the present invention is to provide a motion assist device that can minimize the number of actuators that are required for assisting a certain mode of motion of the user.

A second object of the present invention is to provide a motion assist device that can allow a greater freedom of motion beside from the motion which the motion assist device is designed to assist.

Such objects of the present invention can be accomplished by providing a motion assist device (1; 101) for assisting a motion of a body part of a user (U), comprising: a support member (3, 4, 5, 6; 110) extending in a prescribed direction, and configured to be worn by a first body part of the user; a first link member (10; 105, 106) connected to a first end of the support member so as to be rotatable around a first axial line (A; A1) and configured to be worn by a second body part of the user; a second link member (10; 111) connected to a second end of the support member so as to be rotatable around a second axial line (A; A2) and configured to be worn by a third body part of the user; a drive source (15) mounted on the support member; and a power transmission mechanism for transmitting a power of the drive source to the first link member and the second link member; wherein the power transmission mechanism includes: a rotary arm (21; 121) rotatably supported by the support member at an intermediate point of the rotary arm and driven to rotate by the drive source; a first drive pulley (22; 122) and a second drive pulley (23; 123) supported by one end of the rotary arm so as to be rotatable around a common axial line or mutually parallel axial lines; a third drive pulley (24; 124) and a fourth drive pulley (25; 125) supported by another end of the rotary arm so as to be rotatable around a common axial line or mutually parallel axial lines; a first driven pulley (7L; 107U) fixedly secured to the first link member in a coaxial relationship to the first axial line; a second driven pulley (7R; 107D) fixedly secured to the second link member in a coaxial relationship to the second axial line; a first drive belt (28; 28a; 128) passed around the first driven pulley, the first drive pulley, the third drive pulley and the second drive pulley in that order; and a second drive belt (28; 28b; 128) passed around the second driven pulley, the second drive pulley, the fourth driven pulley and the first driven pulley in that order; wherein the first drive belt is passed around the first drive pulley and the third drive pulley in a cross belt drive, and the second drive belt is passed around the second drive pulley and the fourth drive pulley in a cross belt drive.

When the motion of the user's body part is to be assisted, the rotational motion of the rotary arm is transmitted to the first link member and the second link member via the first drive belt and the second belt, respectively. Thus, the drive torque applied to the rotary arm can be transmitted to the first link member and the second link member so that a prescribed mode of motion of the user's body part is assisted. When the rotary arm is held stationary, and one of the link members is angularly moved, this motion is transmitted to the other link member via the first drive belt and the second drive belt so that the user's body part is enabled to be moved in a mode other than the assisted mode of motion. In other words, the output torque of the drive source can be transmitted to the first link member and the second link member for assisting the prescribed mode of motion of the user's body part while the first link member is permitted to move relative to the second link member for a mode of motion other than the assisted mode of motion so that a differential mechanism is formed.

Typically, the rotary arm is positioned centrally between the first and second driven pulleys, and is provided with a neutral position where a lengthwise direction of the rotary arm is substantially orthogonal to a line connecting the first and second drive pulleys to each other.

According to a preferred embodiment of the present invention, the first drive belt and the second drive belt are passed around both the first driven pulley and the second driven pulley in an open belt drive.

Thereby, the rotational motion of the rotary arm causes a same phase rotary motion of the first driven pulley and the second driven pulley. When the rotary arm is stationary, the first driven pulley and the second driven pulley can rotate in mutually opposite directions.

According to another preferred embodiment of the present invention, the first drive belt and the second drive belt are passed around the first driven pulley in a cross belt drive and the second driven pulley in an open belt drive.

Thereby, the rotational motion of the rotary arm causes opposite phase rotary motions of the first driven pulley and the second driven pulley. When the rotary arm is stationary, the first driven pulley and the second driven pulley can rotate in a same direction.

The motion assist device may further comprise idler pulleys (26) for preventing a slacking of the first drive belt and the second drive belt.

Thereby, the rotational motion of the rotary arm can be transmitted to the first and second driven pulleys without causing any excessive slack or tension in the first and second drive belts.

Preferably, the rotary arm is positioned centrally between the first and second drive pulleys, and is provided with a neutral position where a lengthwise direction of the rotary arm is substantially orthogonal to a line connecting the first and second drive pulleys to each other, and the idler pulleys include a pair of idler pulleys located on either lateral side of the one end of the rotary arm in the neutral position and another pair of idler pulleys located on either lateral side of the other end of the rotary arm in the neutral position, such that the idler pulleys push the drive belts outward.

Thereby, the tension of the first and second drive belts can be controlled in a favorable manner.

The first drive belt and the second drive belt may consist of a single endless drive belt.

Thereby, the structure of the power transmission mechanism can be simplified.

According to a particularly preferred embodiment of the present invention, the first body part is a pelvic part of the user, and the second and third body parts are right and left upper legs of the user.

The same phase motion of the first and second driven pulleys causes opposite phase motions of the upper legs of the user via the first link member and the second link member, respectively, so that the walking motion of the user can be assisted in a favorable manner. At the same time, owing to the differential mechanism included in the power transmission mechanism, the same phase motion of the upper legs of the user is permitted. In other words, the user is allowed to sit or squat or otherwise pivot the hip joints of the user in a same direction.

According to yet another embodiment of the present invention, the first body part is an upper leg of the user, the second body part is a pelvic part of the user, and the third body part is a lower leg of the user.

Thereby, the user is assisted in standing up from a seated position. At the same time, the user is allowed to flex only at the hip joint while the knee joint is kept extended, or to flex only at the knee joint while the hip joint is kept extended.

The first driven pulley and the second driven pulley may have a same diameter. But, the first driven pulley and the second driven pulley may also have different diameters.

In the latter case, by suitably selecting the ratio of the diameters of the first driven pulley and the second driven pulley, a wider range of modes of motion the user can be assisted.

DESCRIPTION OF THE PREFERRED EMBODIMENT(S)

Embodiments of the present invention are described in the following with reference to appended drawings.

First Embodiment

Figure 1:
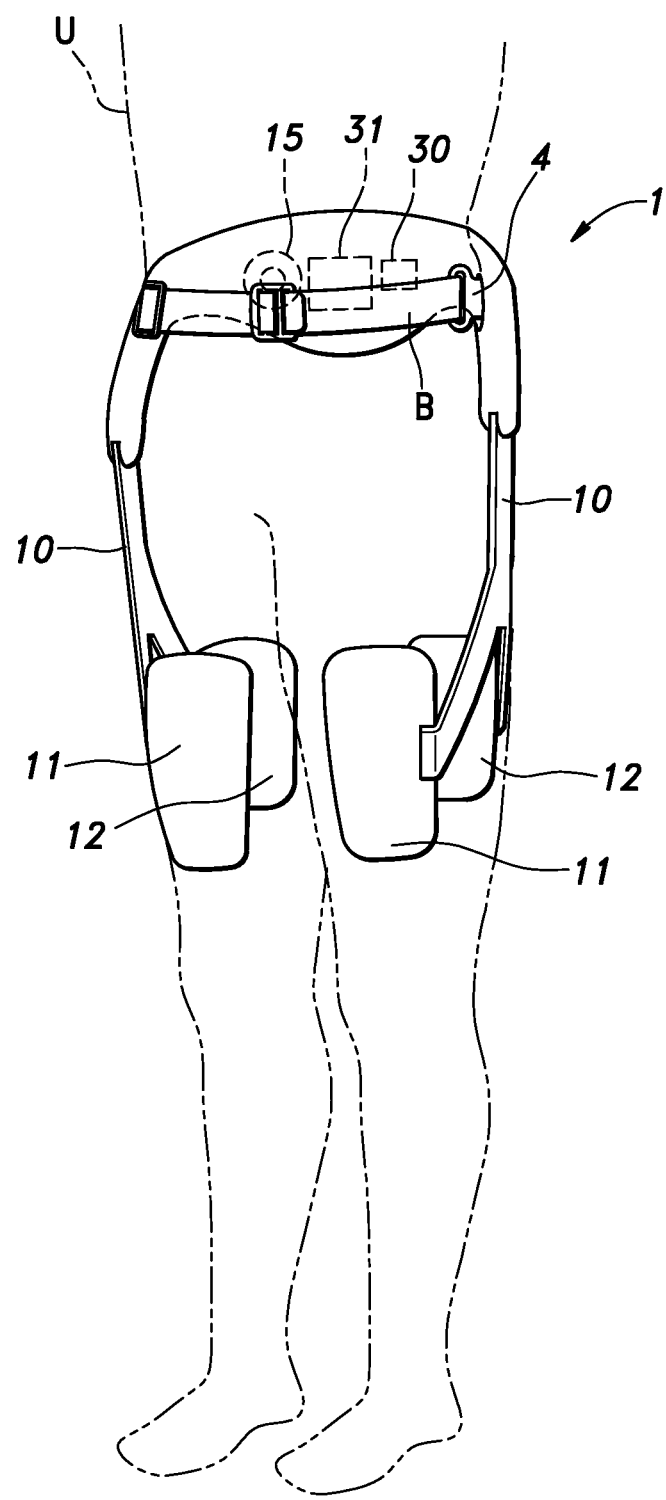
FIG. 1 is a schematic perspective view showing a walking assist device according to a first embodiment of the present invention worn by a user.
Figure 2:
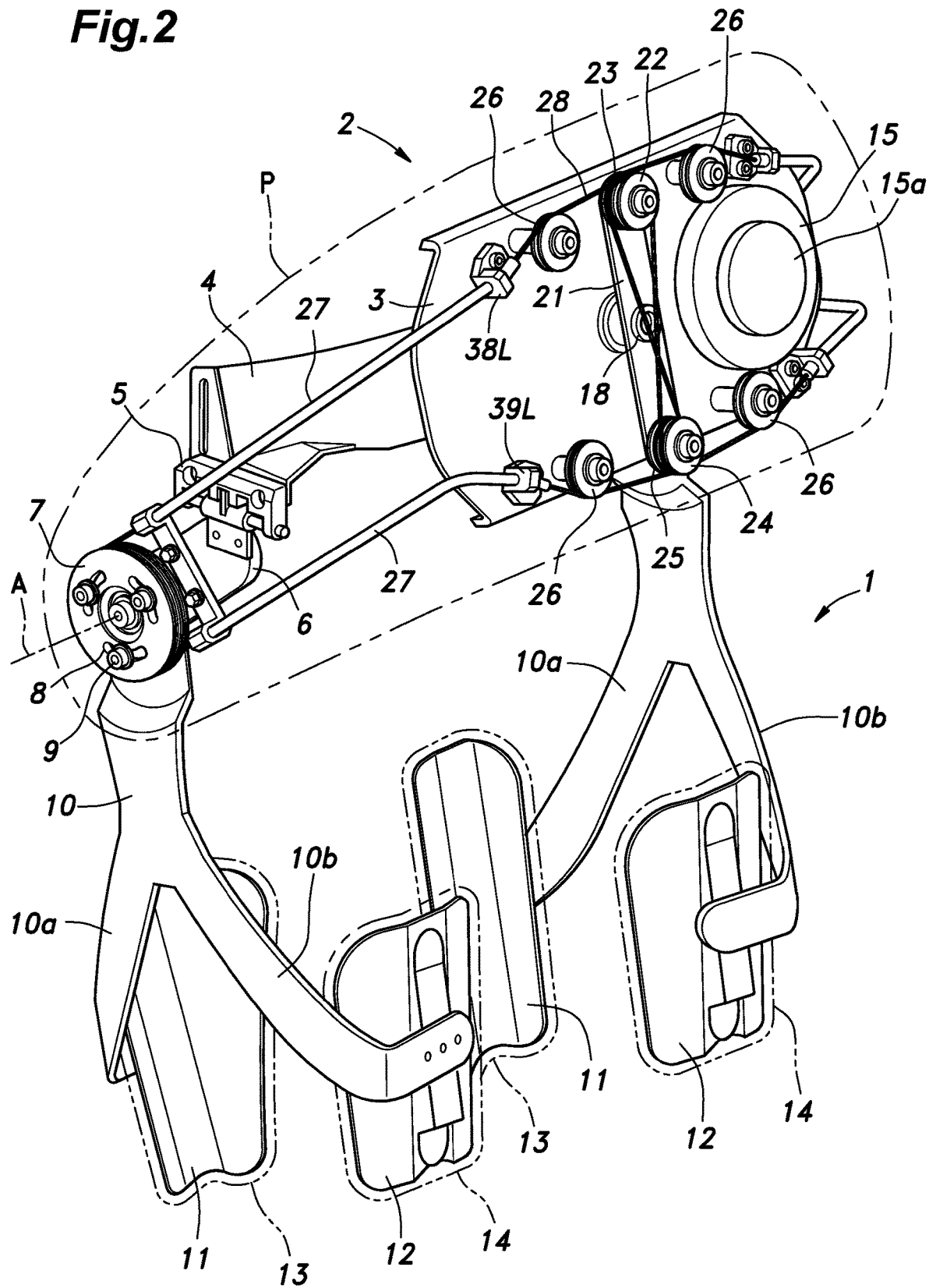
FIG. 2 is a see-through perspective view of the walking assist device as viewed from behind.
Figure 3:
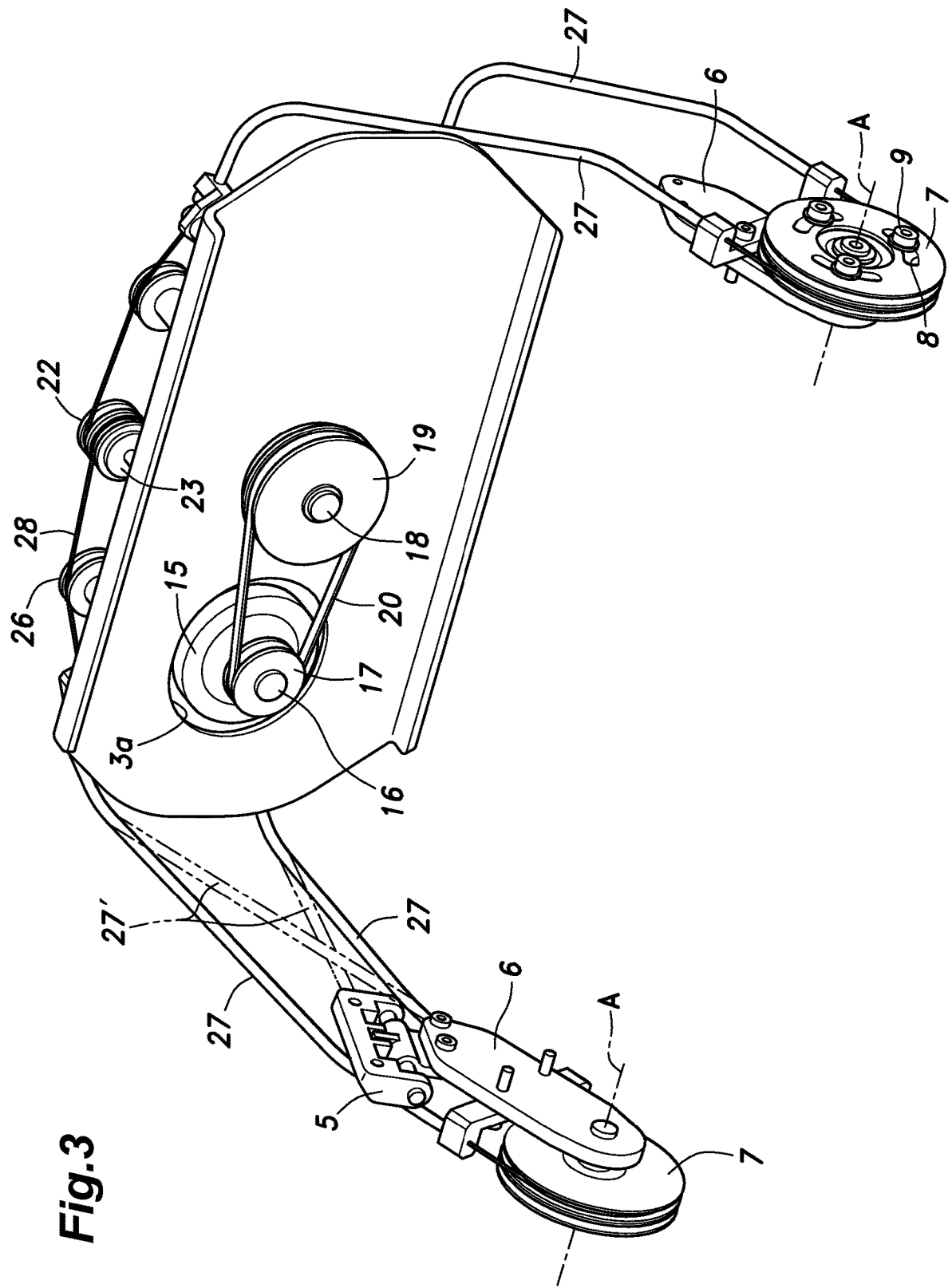
FIG. 3 is a see-through perspective view of a power transmission mechanism of the walking assist device as seen from the front.
Figure 4A:
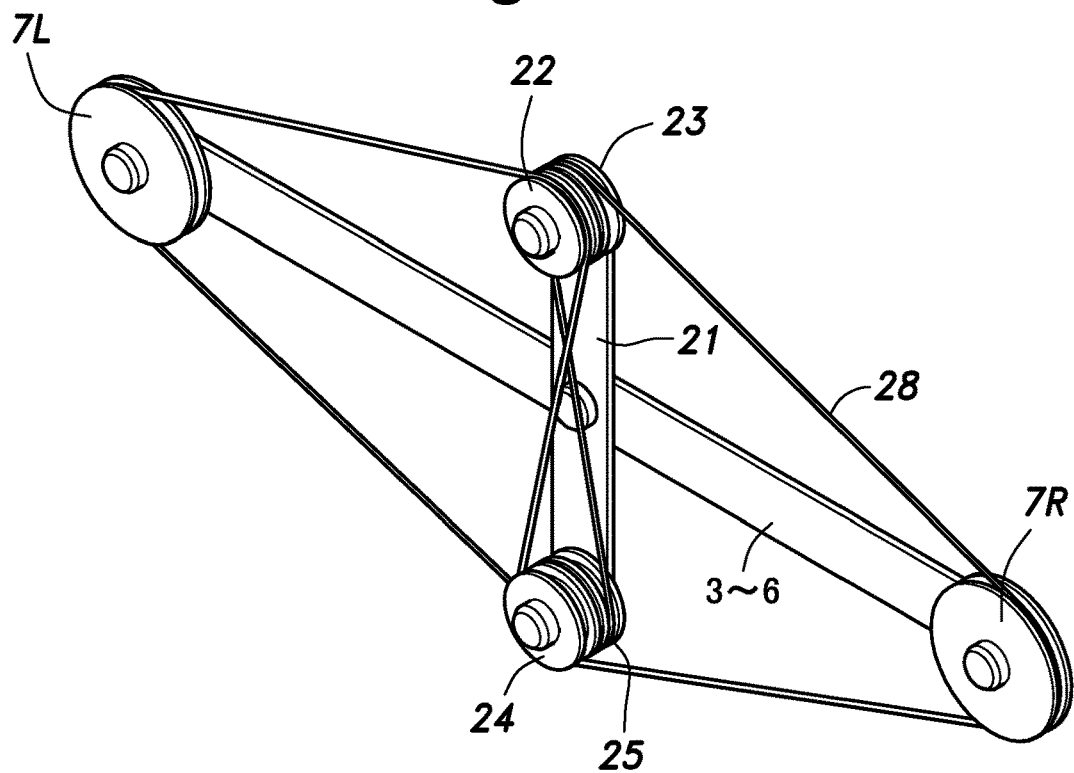
FIG. 4a is a perspective unfolded view of the power transmission mechanism of the walking assist device.
Figure 4B:
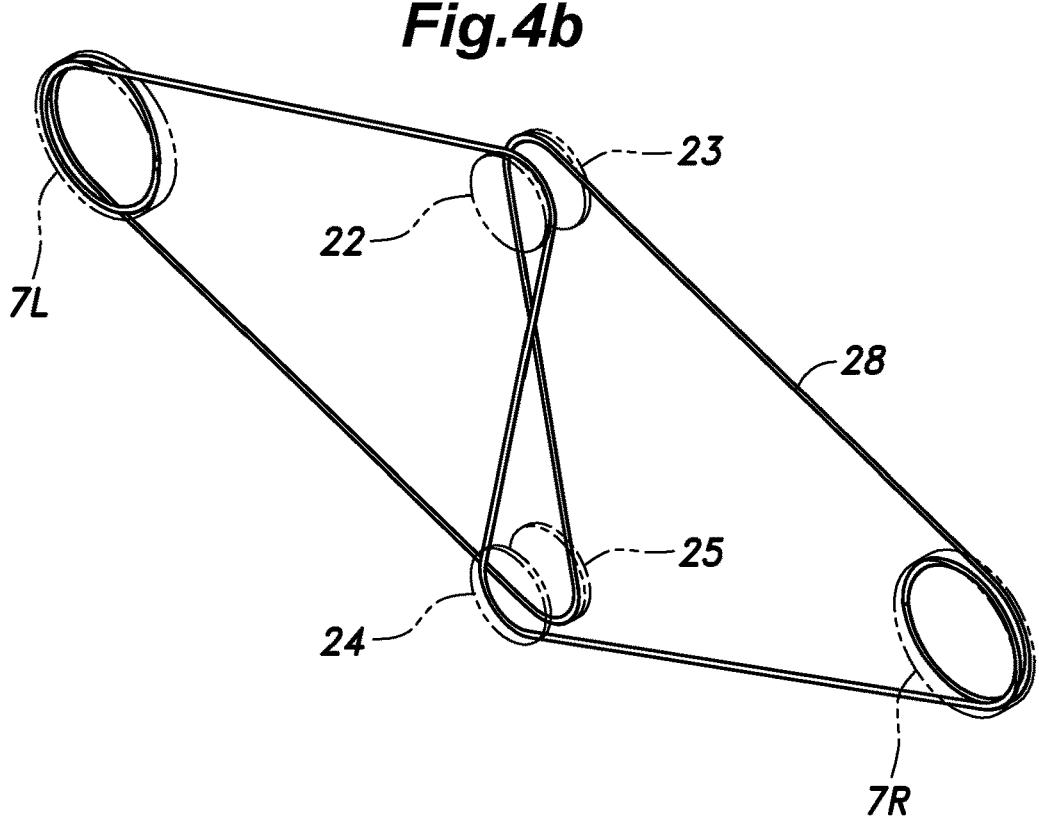
FIG. 4b is a simplified perspective view of a part of the power transmission mechanism.

A walking assist device 1 according to a first embodiment of the present invention is described in the following with reference to FIGS. 1 to 4. FIG. 1 is a schematic perspective view showing the walking assist device according to the first embodiment of the present invention worn by a user U. FIG. 2 is a see-through perspective view of the walking assist device as viewed from behind, and FIG. 3 is a see-through perspective view of a power transmission mechanism of the walking assist device as seen from the front. FIG. 4a is a perspective unfolded view of the power transmission mechanism of the walking assist device. FIG. 4b is a simplified perspective view of a part of the power transmission mechanism.

As shown in FIG. 1, many of the components of the walking assist device 1 are substantially symmetrical with respect to the sagittal plane of the user U. Therefore, only one side of the walking assist device may be discussed in the following disclosure wherever appropriate to avoid redundancy. When any particular component is required to be indicated on which side of the user the component is located, a suffix "L" or "R" is appended to the corresponding numeral.

The walking assist device 1 includes a pelvic support assembly 2 configured to be worn by the user U. The pelvic support assembly 2 includes a back frame 3 consisting of a stiff plate member and positioned on the back side of the user U, a pair of side frames 4 extending forward from either lateral end of the back frame 3, and a belt B detachably connected between the free ends of the side frames 4. The back frame 3 and the side frames 4 are covered by a pad member P so that the pelvic support assembly 2 may be worn by the user U with comfort.

Each side frame 4 is fitted with a hinge member 5 supporting a downwardly extending side member 6 so as to be rotatable around a hinge axis extending in the fore and aft direction. The lower end of the side member 6 is positioned adjacent to the corresponding hip joint of the user U, and supports a driven pulley 7 so as to be rotatable around a laterally extending axial line A. As shown in FIGS. 2 and 3, the driven pulley 7 is provided with three arcuate slots 8 extending circumferentially around the axial line A, and three rods 9 projecting from the side member 6 are passed into the respective arcuate slots 8. Thereby, the angular motion of the driven pulley 7 relative to the side member 6 is limited to a prescribed angular range.

The upper end of a femoral arm 10 is fixedly attached to the driven pulley 7. The lower end of the femoral arm 10 is bifurcated into a front arm 10a and a rear arm 10b. A front femoral plate 11 is attached to the lower end of the front arm 10a, and a rear femoral plate 12 is attached to the lower end of the rear arm 10b so that the front femoral plate 11 and the rear femoral plate 12 oppose the front side and the rear side of the femoral part (upper leg) of the user U. The opposing surfaces of the front femoral plate 11 and the rear femoral plate 12 are provided with suitable pad members 13 and 14, respectively.

The back frame 3 supports an electric motor 15 on the back side thereof, and the output shaft 16 of the electric motor 15 is passed through an opening 3a of the back frame 3, and projects forward. The projecting end (front end) of the output shaft 16 is fitted with a drive pulley 17. The electric motor 15 is provided with an angle sensor 15a for measuring the angular position of the output shaft 16 of the electric motor 15. The back frame 3 supports a control unit 30 for controlling the motion of the electric motor 15 and a battery 31 for powering the electric motor 15 and the control unit 30.

A central part of the back frame 3 rotatably supports a main shaft 18 which is passed through the back frame 3. The front end of the main shaft 18 is fitted with a driven pulley 19, and a power transmission belt 20 is passed around the drive pulley 17 of the output shaft 16 of the electric motor 15 and the driven pulley 19 of the main shaft 18. The rear end of the main shaft 18 is attached to a middle point of a substantially vertically extending rotary arm 21. In this embodiment, the drive pulley 17 is provided with a smaller diameter than the driven pulley 19 so that the rotational motion of the electric motor 15 is transmitted to the rotary arm 21 at a reduced speed.

The upper end of the rotary arm 21 is fitted with a first drive pulley 22 and a second drive pulley 23 having a mutually same diameter in a coaxial relationship (one behind the other) and in an individually rotatable manner. In the illustrated embodiment, the first drive pulley 22 and the second drive pulley 23 are provided on the same side of the rotary arm 21. The lower end of the rotary arm 21 is similarly fitted with a third drive pulley 24 and a fourth drive pulley 25 having a same diameter as the first and second drive pulleys 22 and 23 in a coaxial relationship (one behind the other) and in an individually rotatable manner. In the illustrated embodiment, the third drive pulley 24 and the fourth drive pulley 25 are provided on the same side of the rotary arm 21. Alternatively, the first and second drive pulleys 22 and 23 may be positioned adjacent to each other in a mutually parallel relationship, instead of being coaxial to each other. Likewise, the third and fourth drive pulleys 24 and 25 may be positioned adjacent to each other in a mutually parallel relationship, instead of being coaxial to each other.

As shown in FIGS. 4a and 4b, a cable 28 (drive belt) is passed around one of the driven pulleys 7 or the left driven pulley 7L (first driven pulley), the first drive pulley 22, the third drive pulley 24, the other one of the driven pulleys 7 or the right driven pulley 7R (second driven pulley), the second drive pulley 23, the fourth drive pulley 25 and the left driven pulley 7L, in that order. The cable 28 is passed around the left driven pulley 7L and the first drive pulley 22 in an open belt drive (so that the two pulleys rotate in a same direction). Similarly, the cable 28 is passed around the left driven pulley 7L and the fourth drive pulley 25, around the right driven pulley 7R and the second drive pulley 23, and around the right driven pulley 7R and the third drive pulley 24, in an open belt drive in each case. On the other hand, the cable 28 is passed around the first drive pulley 22 and the third drive pulley 24, and around the fourth drive pulley 25 and the second drive pulley 23, in a cross belt drive in each case (so that the two pulleys rotate in opposite directions in each case).

As shown in FIG. 2, a pair of idler pulleys 26 are provided on the back frame 3 on either lateral side of the first and the second drive pulleys 22 and 23 in a laterally spaced apart relationship in a symmetric arrangement. Similarly, another pair of idler pulleys 26 are provided on the back frame 3 on either lateral side of the third and the fourth drive pulleys 24 and 25 in a laterally spaced apart relationship in a symmetric arrangement.

The idler pulleys 26 guide the cable 28 such that the section of the cable 28 adjoining each end of the rotary arm 21 extends substantially orthogonally to the lengthwise direction of the rotary arm 21 so that the cable 28 is prevented from being excessively slacked or tensioned as the rotary arm 21 undergoes an angular motion over a certain range centered around the vertical neutral position thereof.

As also shown in FIG. 2, a pair of guide pipes 27 are connected between a left side end of the back frame 3 and the left side member 6 by connection members 38L and 39L in a vertically spaced apart relationship. The guide pipes 27 on the left hand side receive the sections of the cable 28 extending between the first drive pulley 22 and the left driven pulley 7L and between the left driven pulley 7L and the fourth drive pulley 25. Likewise, another pair of guide pipes 27 are connected between a right side end of the back frame 3 and the right side member 6 in a vertically spaced apart relationship. The guide pipes 27 on the right hand side receive the sections of the cable 28 extending between the second drive pulley 23 and the right driven pulley 7R and between the right driven pulley 7R and the third drive pulley 24.

The mode of operation of the walking assist device 1 is described in the following. First of all, it is assumed that the two femoral arms 10 are under a substantially equal loading, and the electric motor 15 applies a certain torque to the rotary arm 21 by receiving a supply of electric current from the battery 31 under the control of the control unit 30 so that the user U is assisted by the walking assist device 1 in the user's walking motion.

Figure 5A:
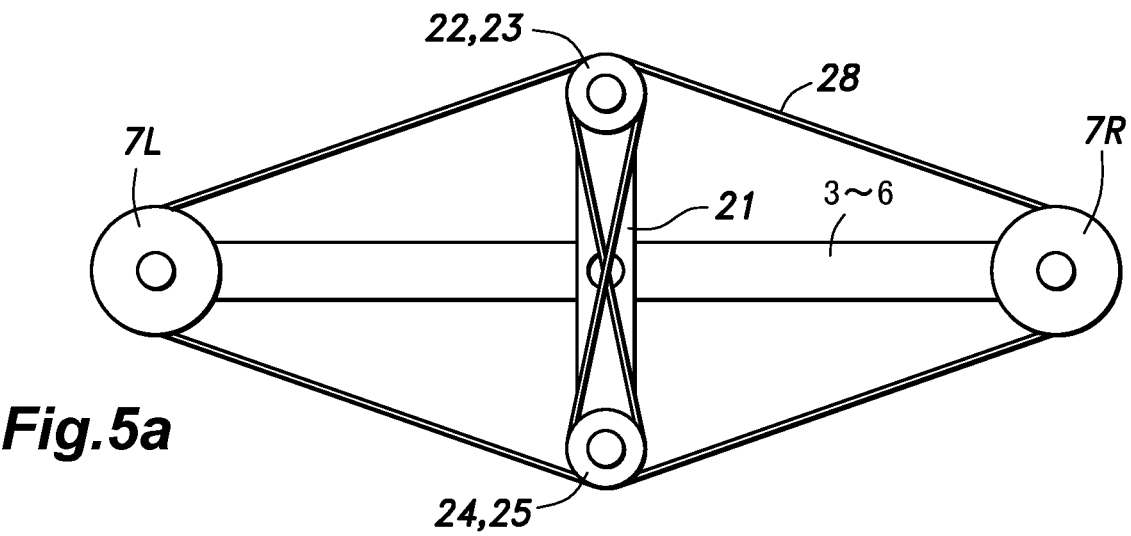
FIG. 5a is a schematic unfolded view of a part of the walking assist device in a neutral state.
Figure 5B:
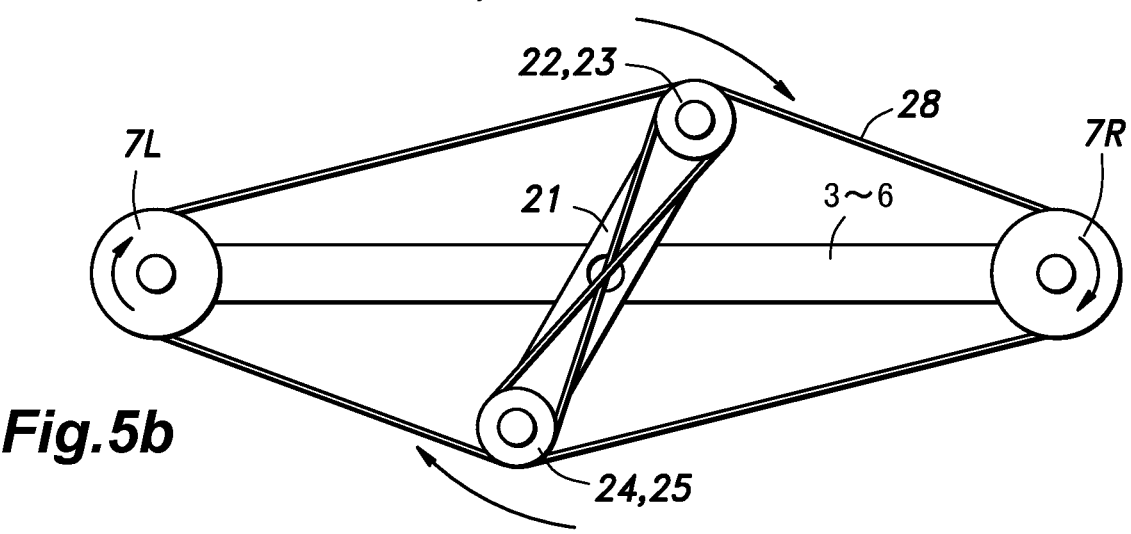
FIG. 5b is a view similar to FIG. 5a when a rotary arm is tilted in one direction.

When the user U stands upright and squarely, the rotary arm 21 is in the vertical (neutral) position, where the lengthwise direction of the rotary arm 21 is substantially orthogonal to a line connecting the left and right driven pulleys 7L and 7R, as shown in FIG. 5a. When the electric motor 15 is actuated so as to tilt the rotary arm 21 in a clockwise direction by a certain angle as shown in FIG. 5b, the torque is transmitted to the left and right driven pulleys 7 via the cable 28 so that the left and right driven pulleys 7 both rotate in clockwise direction. As the driven pulleys 7 are positioned on either side of the user, and are fixedly connected to the corresponding femoral arms 10, the left femoral arm 10L swings forward while the right femoral arm 10R swings rearward, or the two femoral arms undergo opposite phase motions.

Figure 5C:
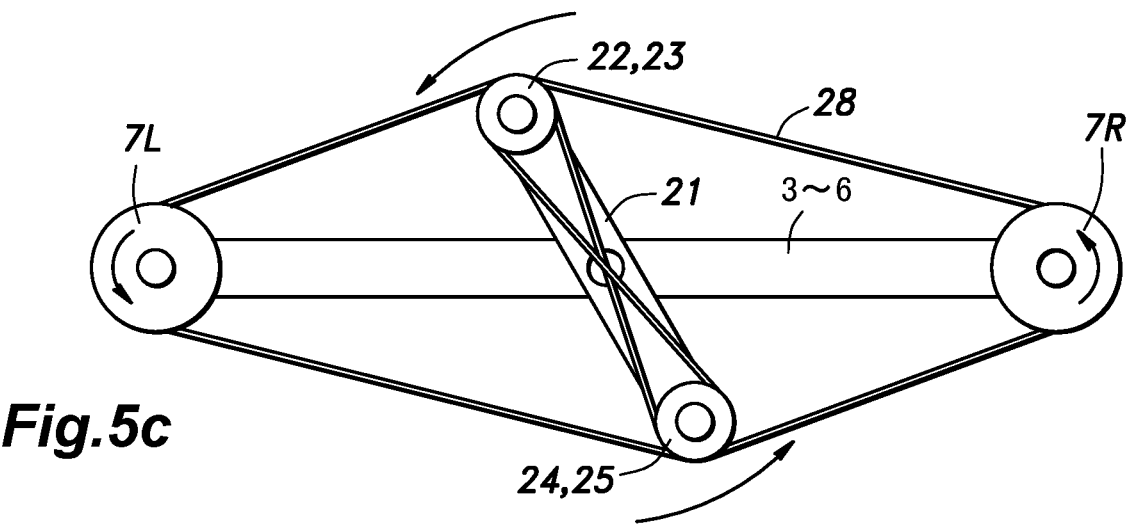
FIG. 5c is a view similar to FIG. 5a when the rotary arm is tilted in the other direction.

Conversely, when the electric motor 15 is actuated so as to tilt the rotary arm 21 in a counterclockwise direction by a certain angle as shown in FIG. 5c, the torque is transmitted to the left and right driven pulleys 7 via the cable 28 so that the left and right driven pulleys 7 both rotate in counterclockwise direction. As the driven pulleys 7 are positioned on either side of the user, and are fixedly connected to the corresponding femoral arms 10, the left femoral arm 10L swings rearward while the right femoral arm 10R swings forward, or the two femoral arms undergo opposite phase motions.

In this manner, by applying a torque from the electric motor 15 to the femoral arms 10 in alternating directions, the walking motion of the user is assisted by the walking assist device 1.

Figure 6:
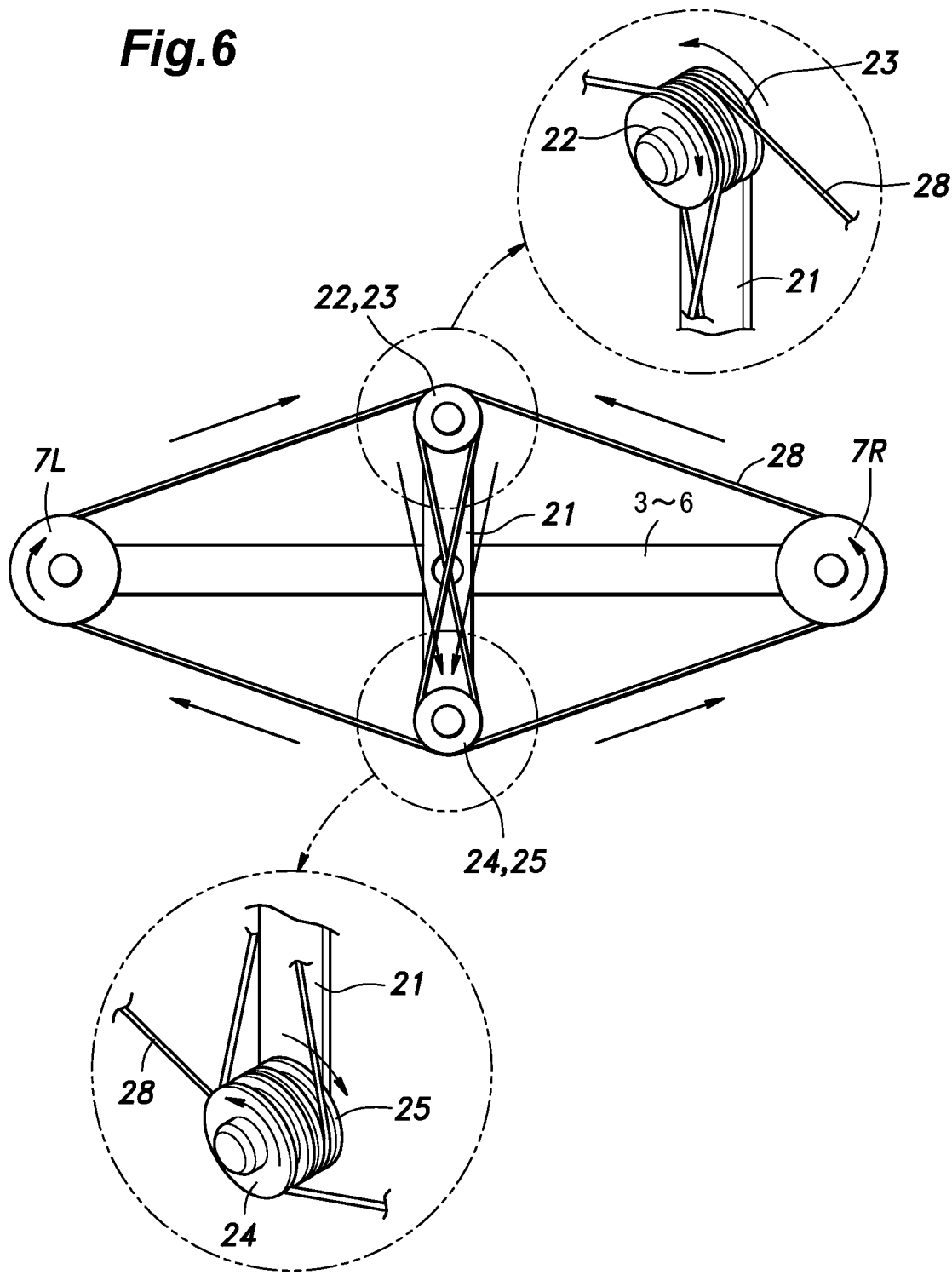
FIG. 6 is a diagram illustrating a same phase extending motion of the power transmission mechanism.

When the user U moves the upper legs in a same direction, for instance, by sitting or squatting from an upright posture, the femoral arms 10 are swung in the same direction. More specifically, the left driven pulley 7L is rotated in clockwise direction while the right driven pulley 7R is rotated in counterclockwise direction (while the rotary arm 21 remains in the vertical position) as shown in FIG. 6. This is permitted because the rotations of the drive pulleys 22 to 25 accommodate the travel of the cable 28 caused by the rotation of the two driven pulleys 7 in opposite directions.

Figure 7:
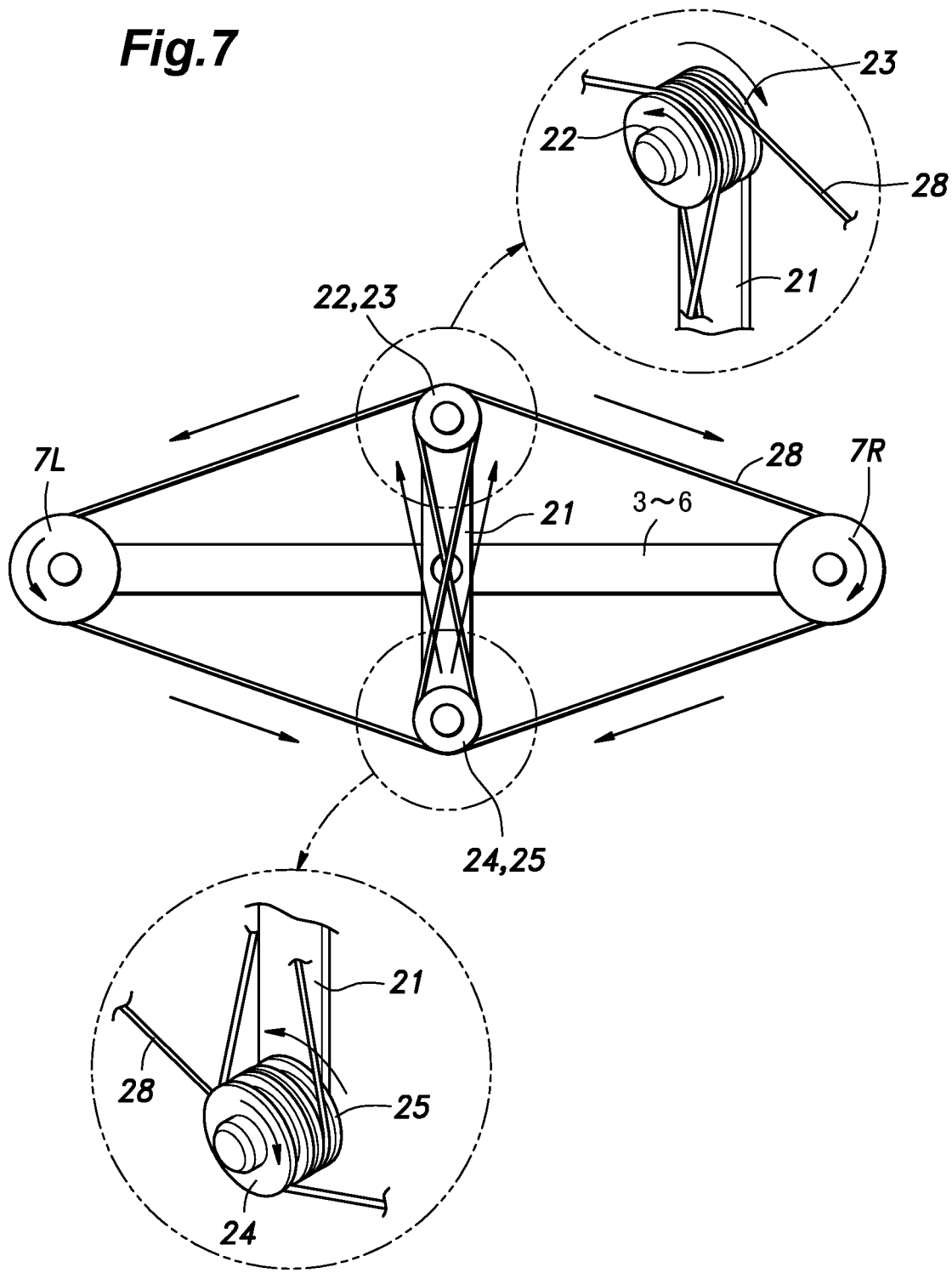
FIG. 7 is a view similar to FIG. 6 illustrating a same phase bending motion of the power transmission mechanism.

When the user U moves the upper legs in a same direction by standing upright from a sitting or squatting posture also, the femoral arms 10 are swung in the same direction. More specifically, the left driven pulley 7L is rotated in counterclockwise direction while the right driven pulley 7R is rotated in clockwise direction (while the rotary arm 21 remains in the vertical position) as shown in FIG. 7. This is permitted again because the rotations of the drive pulleys 22 to 25 accommodate the travel of the cable 28 caused by the rotation of the two driven pulleys 7 in opposite directions.

In other words, according to the illustrated embodiment, the flexing of the hip joints in a same direction, such as when standing upright from a sitting posture or sitting down from an upright posture, can be accomplished without rotating the electric motor 15 or without being hampered by the resistance of the electric motor 15.

In the actual operation of the walking assist device 1, the assisting action of the walking assist device 1 and the same phase motion of the hip joints (or the upper legs) may occur at the same time as a combined motion. Owing to the differential mechanism that allows the same phase motion of the upper legs of the user U, the user U can receive the assisting force from the walking assist device 1 in a comfortable manner.

The control unit 30 consists of an electric circuit unit including CPU, RAM, ROM and a peripheral circuit, and performs a computation process according to a computer program stored in the memory. The control unit 30 may be attached to the back frame 3 or otherwise incorporated in the pelvic support assembly 2. The battery 31 may also be supported by the back frame 3 in a detachable manner for recharging purpose.

Figure 8:
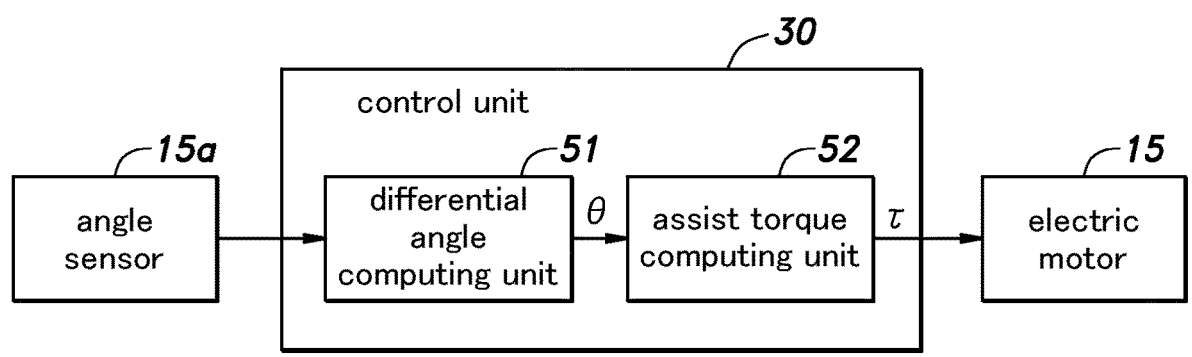
FIG. 8 is functional block diagram of a control unit of the walking assist device.

As shown in FIG. 8, the control unit 30 includes a differential angle computing unit 51 for computing a differential angle $\theta$ between the right and left femoral arms 10 according to the detection signal of the angle sensor 15a, and an assist torque computing unit 52 for computing an assist torque $\tau$ to be applied to the femoral parts of the user U according to the differential angle $\theta$ computed by the differential angle computing unit 51. The electric current corresponding to the computed assist torque $\tau$ is supplied to the electric motor 15.

Figure 9:
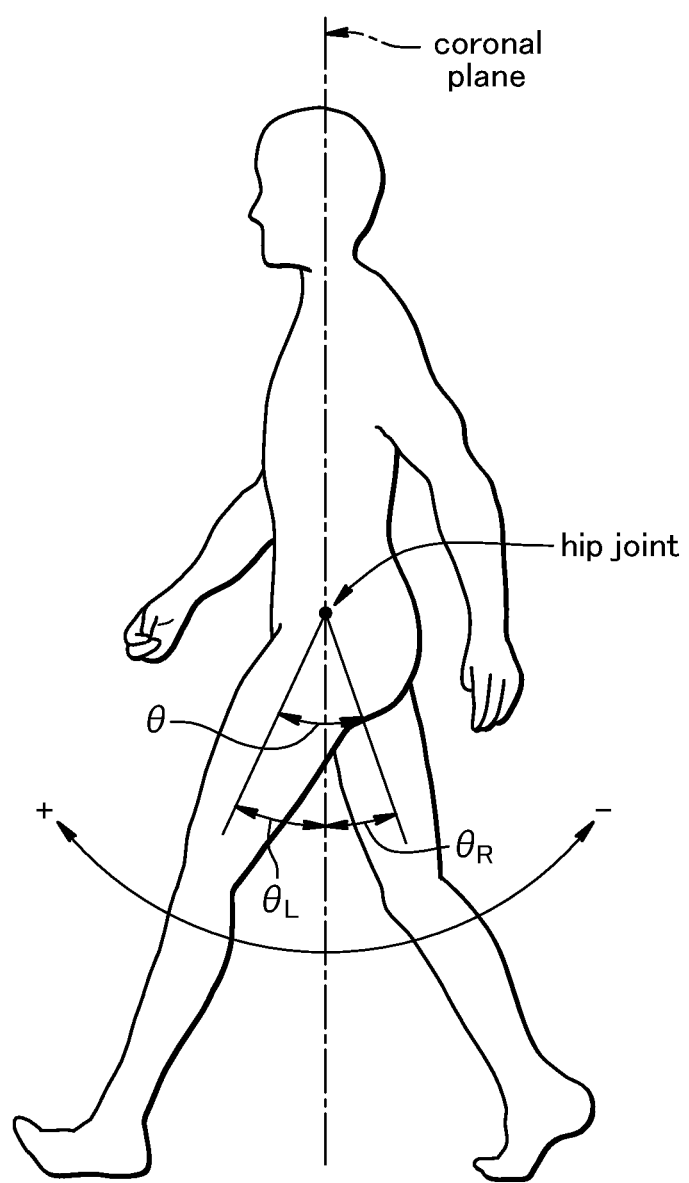
FIG. 9 is a diagram illustrating the definition of a differential angle.

As shown in FIG. 9, the differential angle $\theta$ is defined as a difference between the left and right hip joint angles $\theta L$ and $\theta R$. The hip joint angle is positive when the upper leg is bent forward, and negative when extended rearward relative to a coronal plane. In the illustrated embodiment, the differential angle is positive when the left leg is ahead of the right leg.

In the present embodiment, the assist torque computing unit 52 computes a differential angular speed $\omega$ from the differential angle $\theta$ computed by the differential angle computing unit 51, and computes a differential angle phase $\phi$ in the phase plane of the differential angle $\theta$ and the differential angular speed $\omega$. The torque $\tau$ to be applied to the upper legs of the user U is computed from the differential angle phase $\phi$.

Alternatively, the assist torque computing unit 52 computes a differential angular speed $\omega$ and a walking frequency from the differential angle $\theta$ computed by the differential angle computing unit 51, and computes a differential angle phase $\phi$ in the phase plane of the differential angle $\theta$ and the differential angular speed $\omega$, and an oscillator phase $\phi c$ of a phase oscillator that oscillates in synchronism with the differential angle phase $\phi$ at a natural frequency corresponding to the walking frequency. The torque $\tau$ to be applied to the upper legs of the user U is computed from the differential angle phase $\phi$ and the oscillator phase $\phi c$. For details of such control processes, reference may be made to US2016/0338897A1.

When the two upper legs of the user U undergo opposite phase motions, the assist torque computing unit 52 computes the assist torque $\tau$ that corresponds to the differential angle $\theta$. When the two upper legs of the user U undergo same phase motions, as no differential angle $\theta$ is produced, the assist torque computing unit 52 computes zero assist torque, and the electric motor 15 does not apply any torque to the rotary arm 21.

Modifications of First Embodiment

Figure 10:
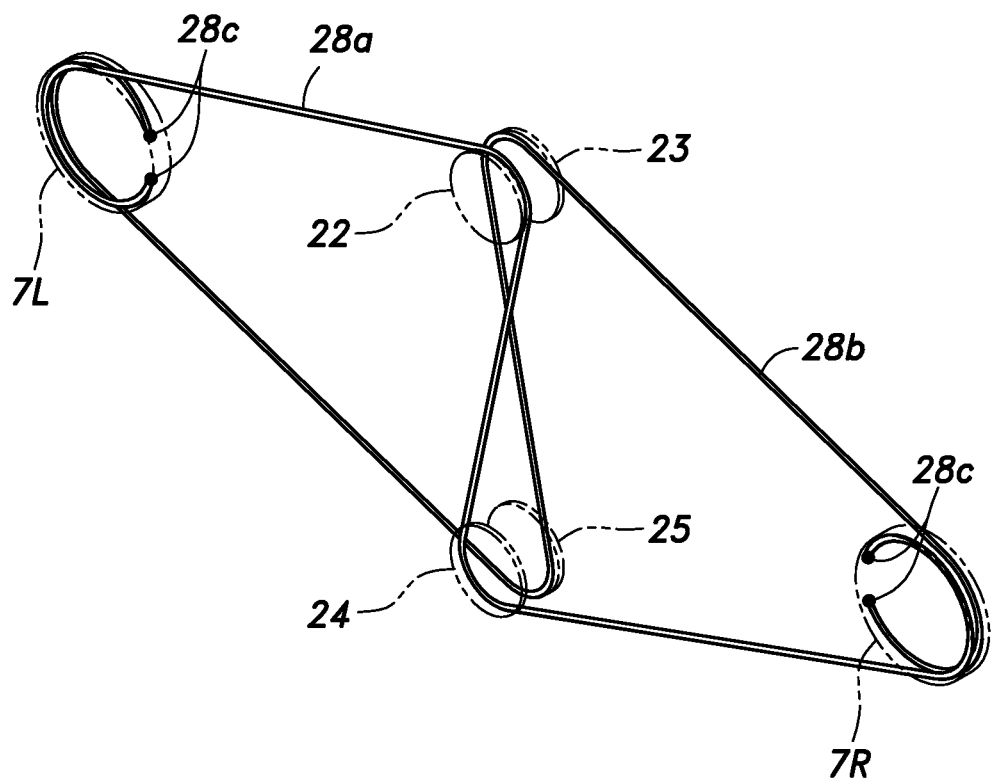
FIG. 10 is a simplified perspective view of a part of the power transmission mechanism according to a first modification of the first embodiment.

In the first embodiment, the cable 28 consisted of a single length of cable. However, the cable 28 may be separated into two parts 28a, 28b as shown in FIG. 10 as a first modification of the first embodiment. In this modification, the first part 28a (first drive belt) of the cable 28 is fixedly attached to the left driven pulley 7L at one end 28c thereof, and after being passed around the left driven pulley 7L (in clockwise direction), the first drive pulley 22, the third drive pulley 24 and the right driven pulley 7R (in counterclockwise direction), is fixedly attached to the right driven pulley 7R at the other end 28c thereof. Similarly, the second part 28b (second drive belt) of the cable 28 may be fixedly attached to the right driven pulley 7R at one end 28c thereof, and after being passed around the right driven pulley 7R (in counterclockwise direction), the second drive pulley 23, the fourth drive pulley 25 and the left driven pulley 7L (in clockwise direction), is fixedly attached to the left driven pulley 7L at the other end thereof.

Figure 11:
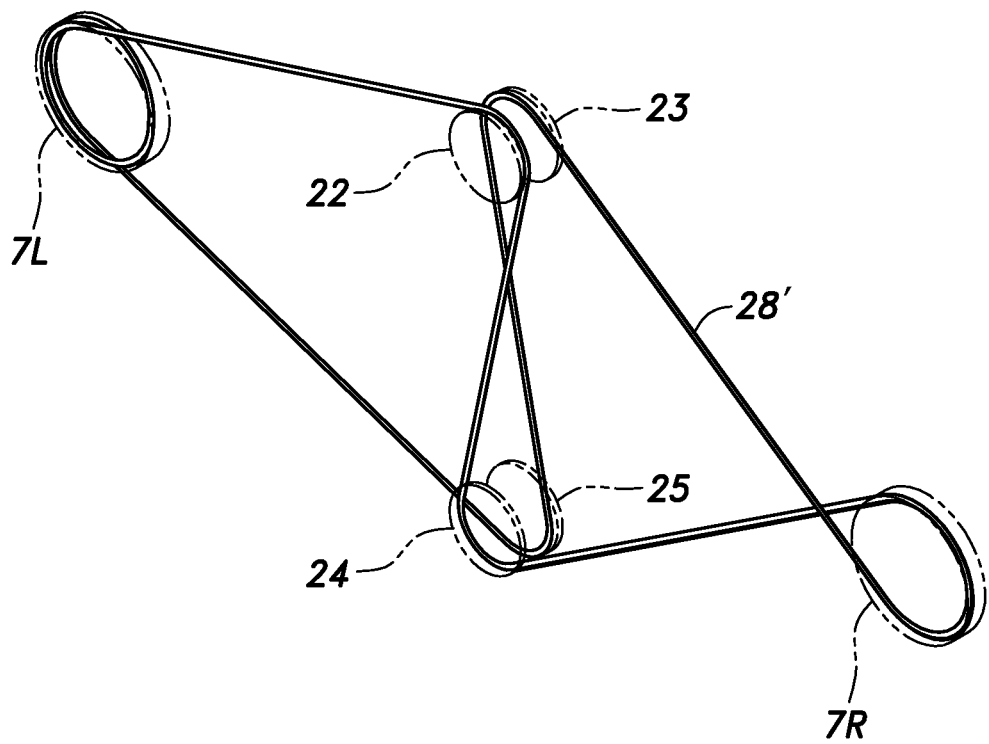
FIG. 11 is a view similar to FIG. 10 showing a second modification of the first embodiment.

FIG. 11 shows a second modification of the first embodiment. The second modification is similar to the first embodiment except for that the cable 28' is passed around the right driven pulley 7R and the second drive pulley 23, and around the right driven pulley 7R and third drive pulley 24 in a cross belt drive in each case, instead of an open belt drive. The guide pipes 27' for the cable 28' are shown in FIG. 3 in imaginary lines.

Therefore, as the rotary arm 21 rotates in either direction, the right and left driven pulleys 7R and 7L rotate in mutually opposite directions. As a result, the right and left femoral arms 10R and 10L swing in a same direction. Therefore, the walking assist device 1 in this case assists the same phase motion of the hip joints such as when standing up upright from a sitting posture, and when sitting from an upright posture.

When the right and left upper legs are moved in mutually different directions, or when the user U is walking in a normal fashion so as to swing the right and left femoral arms 10R and 10L in opposite directions, the user U is allowed to do so without being hampered by the resistance of the electric motor 15. More specifically, when the left driven pulley 7L is rotated in clockwise direction, the right driven pulley 7R is allowed to be rotated also in clockwise direction. This is permitted because the rotations of the drive pulleys 22 to 25 accommodate the travel of the cable 28' caused by the rotation of the two driven pulleys 7 in the same direction.

Second Embodiment

FIGS. 12 to 15 show a rising assist device according to a second embodiment of the present invention. The rising assist device 101 is configured to assist a rising or standing up motion of a user U from a sitting posture.

Figure 12:
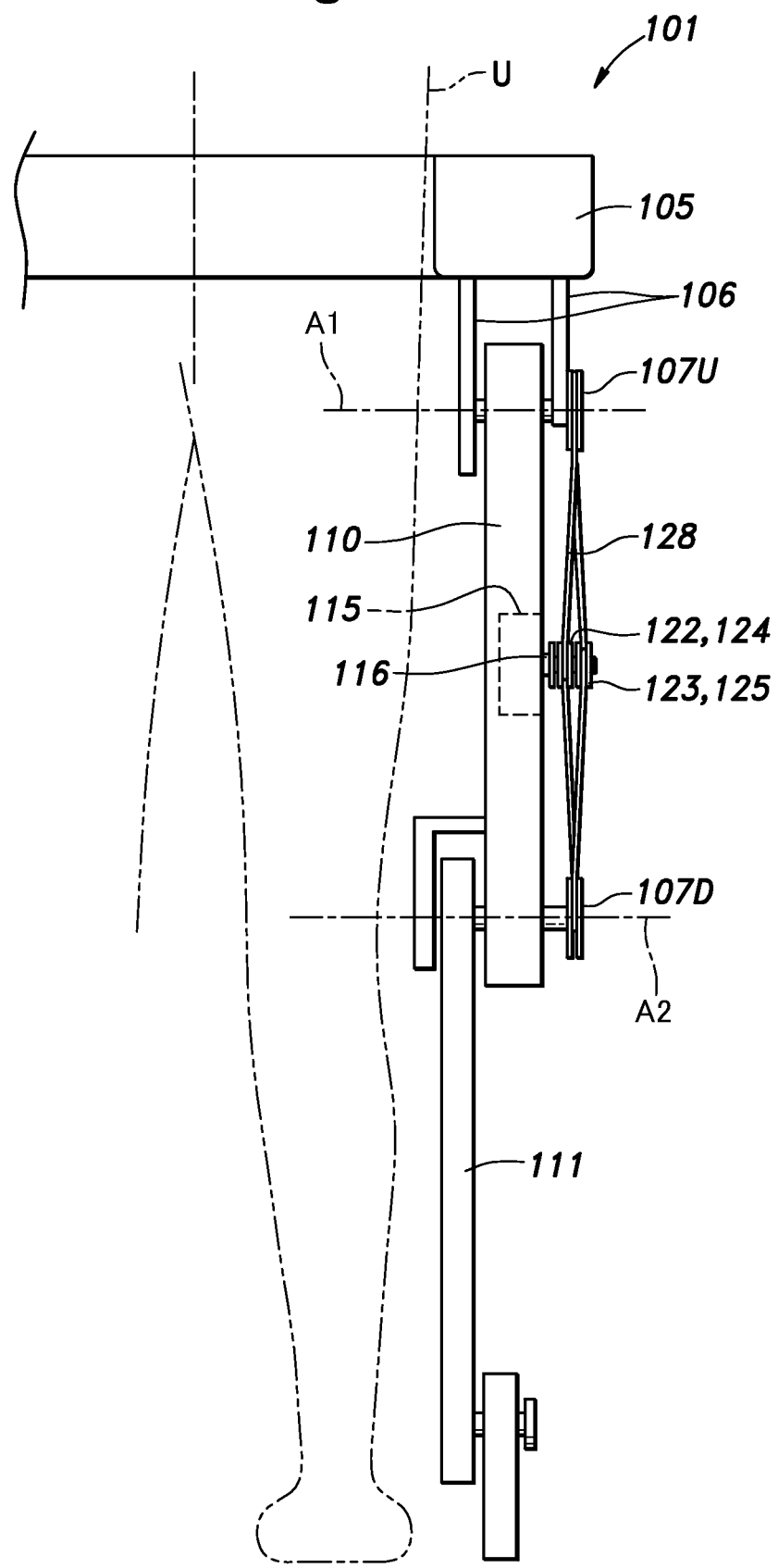
FIG. 12 is a schematic front view showing a left half of a rising assist device according to a second embodiment of the present invention worn by a user.
Figure 13:
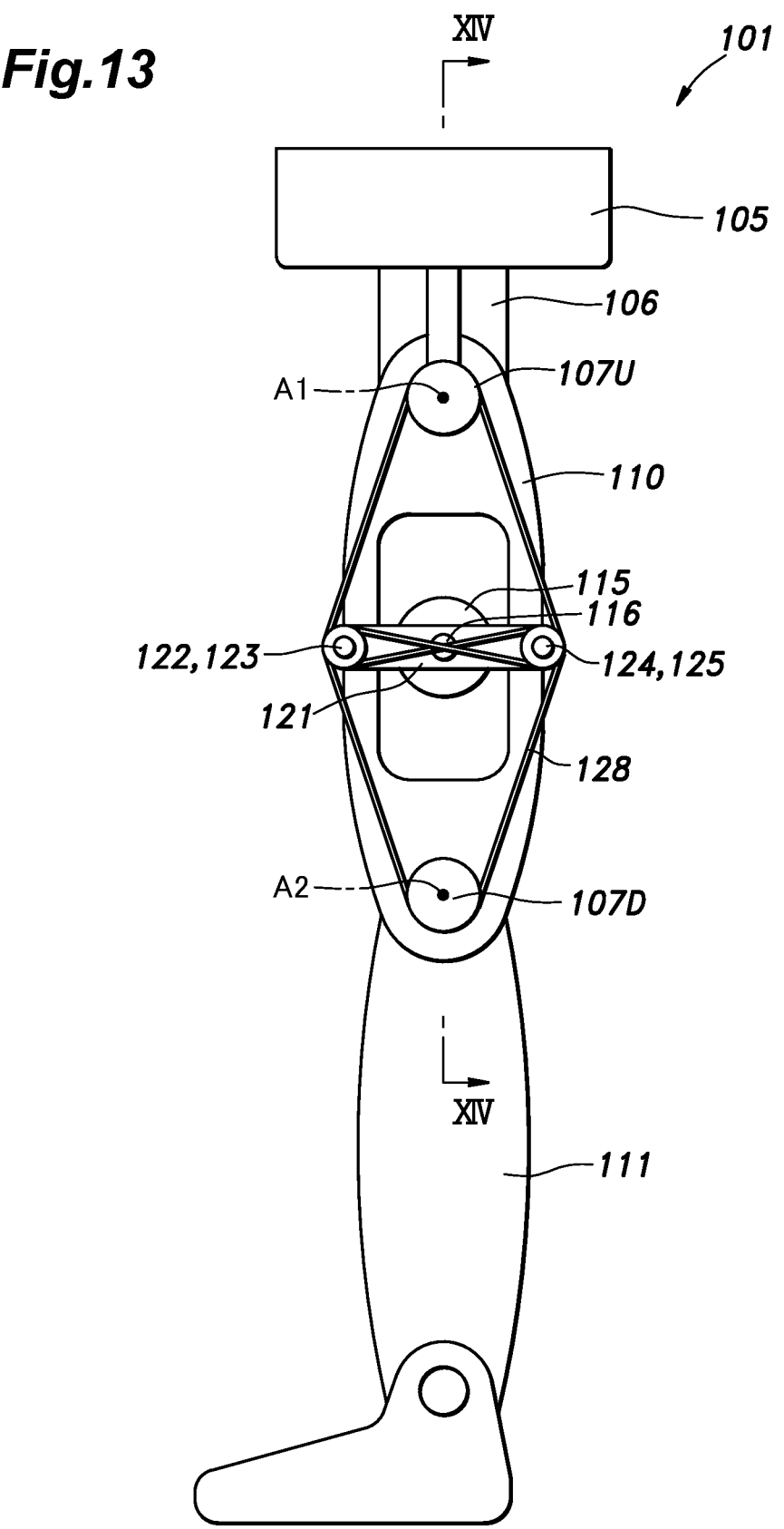
FIG. 13 is a left side view of the rising assist device.
Figure 14:
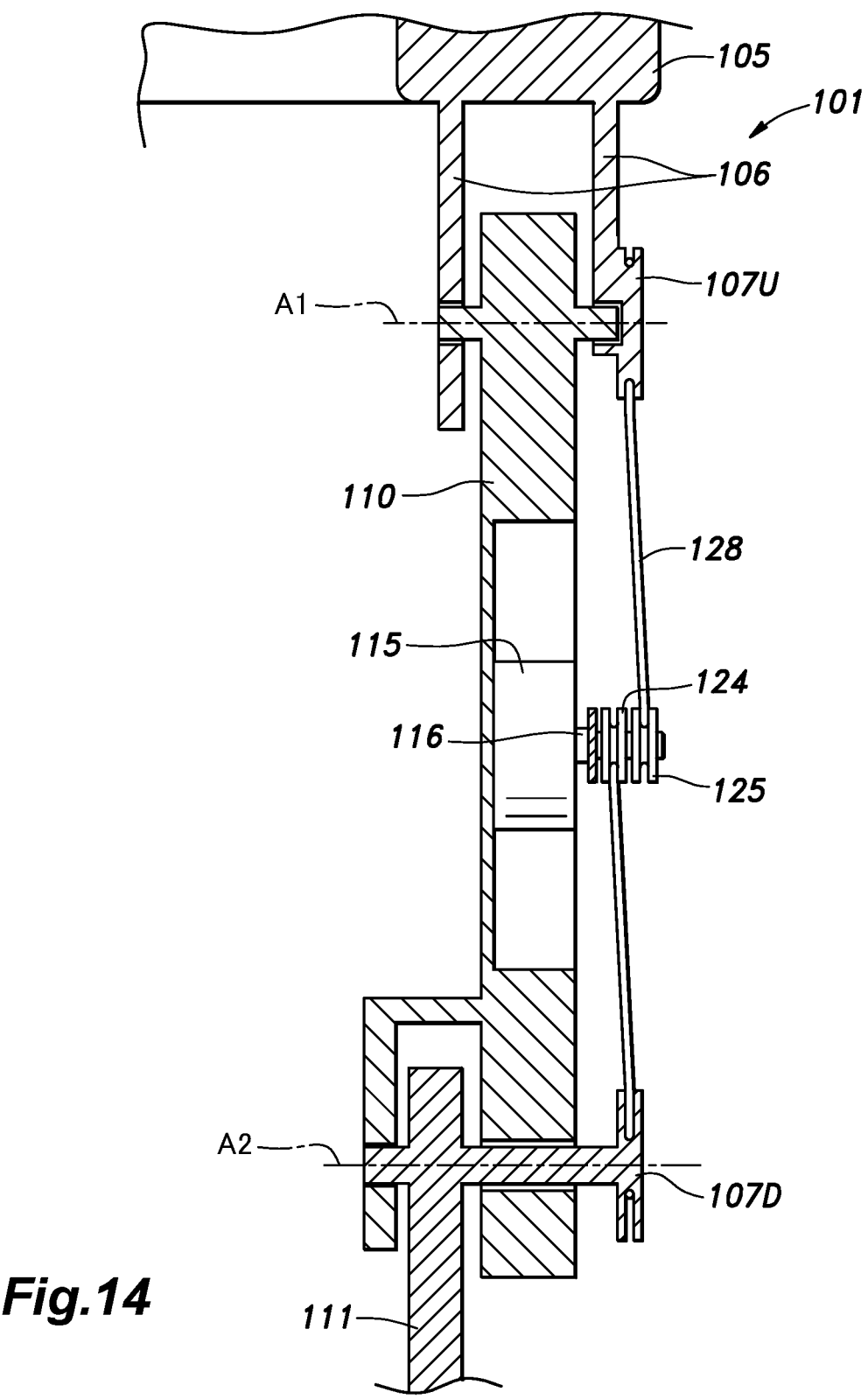
FIG. 14 is a fragmentary sectional view taken along line XIV-XIV of FIG. 13.

FIG. 12 is a schematic front view showing a left half of the rising assist device 101, and FIG. 13 is a left side view of the rising assist device 101. FIG. 14 is a sectional view taken along line XIV-XIV of FIG. 13.

The rising assist device 101 includes a pelvic support member 105 configured to be worn by a pelvic part of the user U, an upper leg member 110 pivotally supported by a side member 106 depending from the pelvic support member 105 so as to be rotatable around a laterally extending first axial line A1 substantially aligned with the hip joint of the user U and configured to be secured to the upper leg of the user, and a lower leg member 111 connected to the lower end of the upper leg member 110 so as to be rotatable around a laterally extending second axial line A2 substantially aligned with the knee joint of the user U and configured to be secured to the lower leg of the user.

The lower end of the side member 106 is integrally provided with an upper driven pulley 107U disposed coaxially with the first axial line A1. A rotary arm 121 extending in the fore and aft direction is pivotally attached to a vertically middle point of the upper leg member 110 via a main shaft 116. A first drive pulley 122 and a second drive pulley 123 are rotatably attached to the front end of the rotary arm 121 in a mutually coaxial relationship. A third drive pulley 124 and a fourth drive pulley 125 are rotatably attached to the rear end of the rotary arm 121 in a mutually coaxial relationship. The upper end of the lower leg member 111 is integrally provided with a lower driven pulley 107D disposed coaxially with the second axial line A2.

A cable 128 is passed around the upper driven pulley 107U, the first drive pulley 122, the third drive pulley 124, the lower driven pulley 107D, the second drive pulley 123, the fourth drive pulley 125 and the upper driven pulley 107U, in that order. The cable 128 is passed around the upper driven pulley 107U and the first drive pulley 122 in an open belt drive (so that the two pulleys rotate in a same direction) Similarly, the cable 128 is passed around the upper driven pulley 107U and the fourth drive pulley 125, around the lower driven pulley 107D and the second drive pulley 123, and around the lower driven pulley 107D and the third drive pulley 124, in an open belt drive in each case. On the other hand, the cable 128 is passed around the first drive pulley 122 and the third drive pulley 124, and around the fourth drive pulley 125 and the second drive pulley 123, in a cross belt drive in each case (so that the two pulleys rotate in opposite directions in each case).

Figure 15:
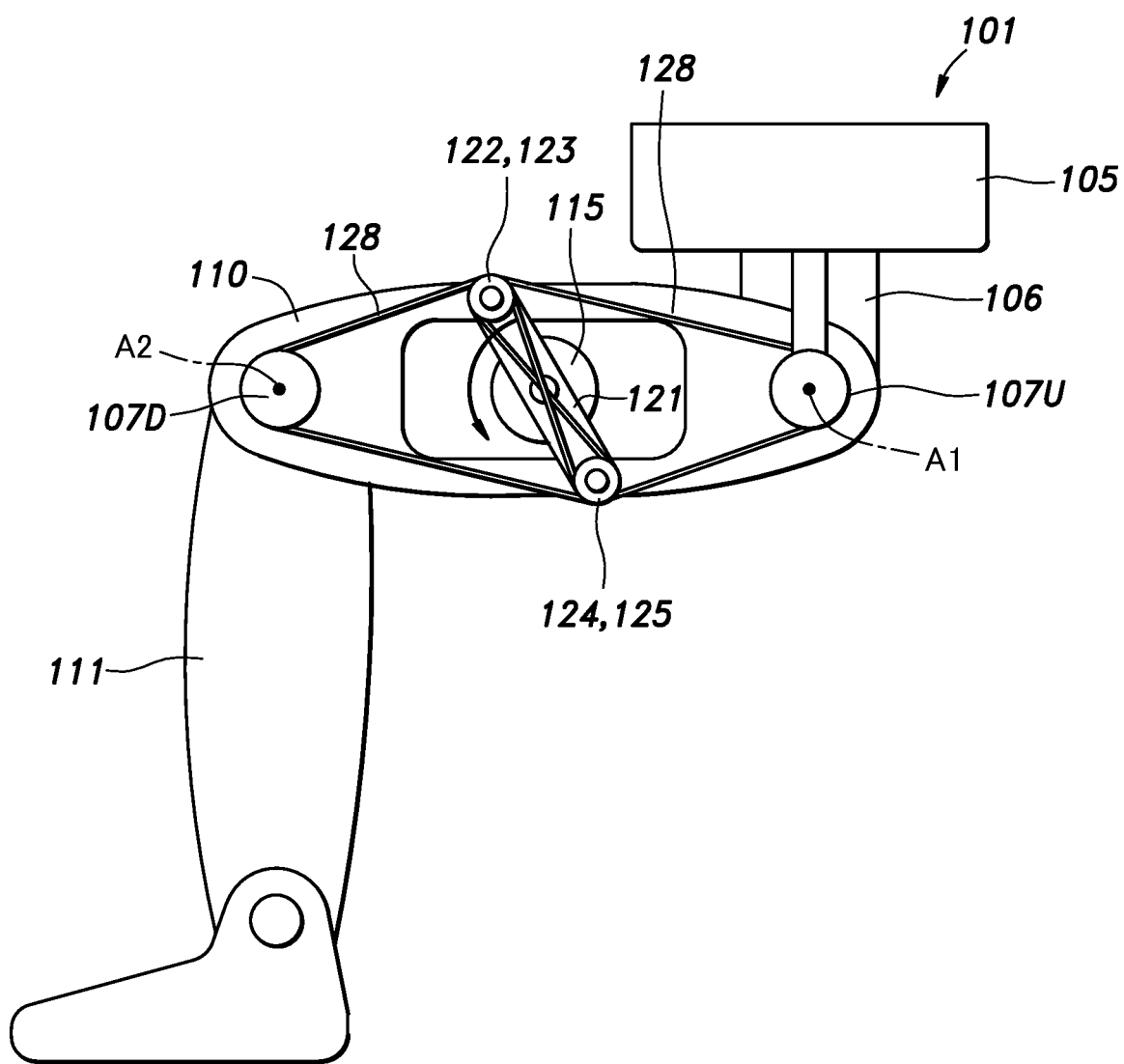
FIG. 15 is a view similar to FIG. 13 when the user is in a sitting posture with both the hip joint and the knee joint of the user flexed.

The mode of operation of the rising assist device 101 is described in the following with reference to FIGS. 13 and 15. FIG. 15 is a view similar to FIG. 13 showing the rising assist device 101 when both the hip joint and the knee joint of the user U are flexed.

First of all, suppose that the user U is standing upright as shown in FIG. 13. When the rotary arm 121 is turned around the main shaft 116 by the electric motor 115 in counterclockwise direction, this causes both the upper driven pulley 107U and the lower driven pulley 107D to turn in counterclockwise direction. Since the pelvic support member 105 is fixed to the user U, the upper leg member 110 rotates forward around the first axial line A1 to be tilted relative to the vertical direction, while the lower leg member 111 rotates rearward relative to the upper leg member 110 around the second axial line A2. The net result is that the upper leg member 110 is tilted horizontally, and the lower leg member 111 maintains the vertical attitude (translational movement) as shown in FIG. 15. When the rotation of the rotary arm 121 is reversed, the upper leg member 110 and the lower leg member 111 are moved to return to their respective original upright attitude to assist rising of the user U from the sitting posture.

In this manner, the rising assist device 101 of the illustrated embodiment is able to assist the user U to stand upright from the sitting posture.

When the user U stoops forward from the upright posture (bends the hip joint and keeps the knee joint extended), the upper driven pulley 107U rotates relative to the upper leg member 110. This causes the cable 128 to travel in the lengthwise direction thereof so that the stooping motion of the user U or the rotation of the upper driven pulley 107U is permitted by the rotation of the first to fourth drive pulleys 122 to 125 and the lower driven pulley 107D.

Similarly, when the user U throws the leg rearward while keeping the hip joint extended, the lower driven pulley 107D rotates relative to the upper leg member 110. This causes the cable 128 to travel in the lengthwise direction thereof so that the rearward kicking motion of the user U or the rotation of the lower driven pulley 107D is permitted by the rotation of the first to fourth drive pulleys 122 to 125 and the upper driven pulley 107U. In a similar fashion, the user U is enabled to squat (to bend both the hip joint and the knee joint) from an upright posture without being hampered by the electric motor 115. In short, the user U is enabled to flex the hip joint and the knee joint independently from each other.

Modifications of Second Embodiment

Figure 16:
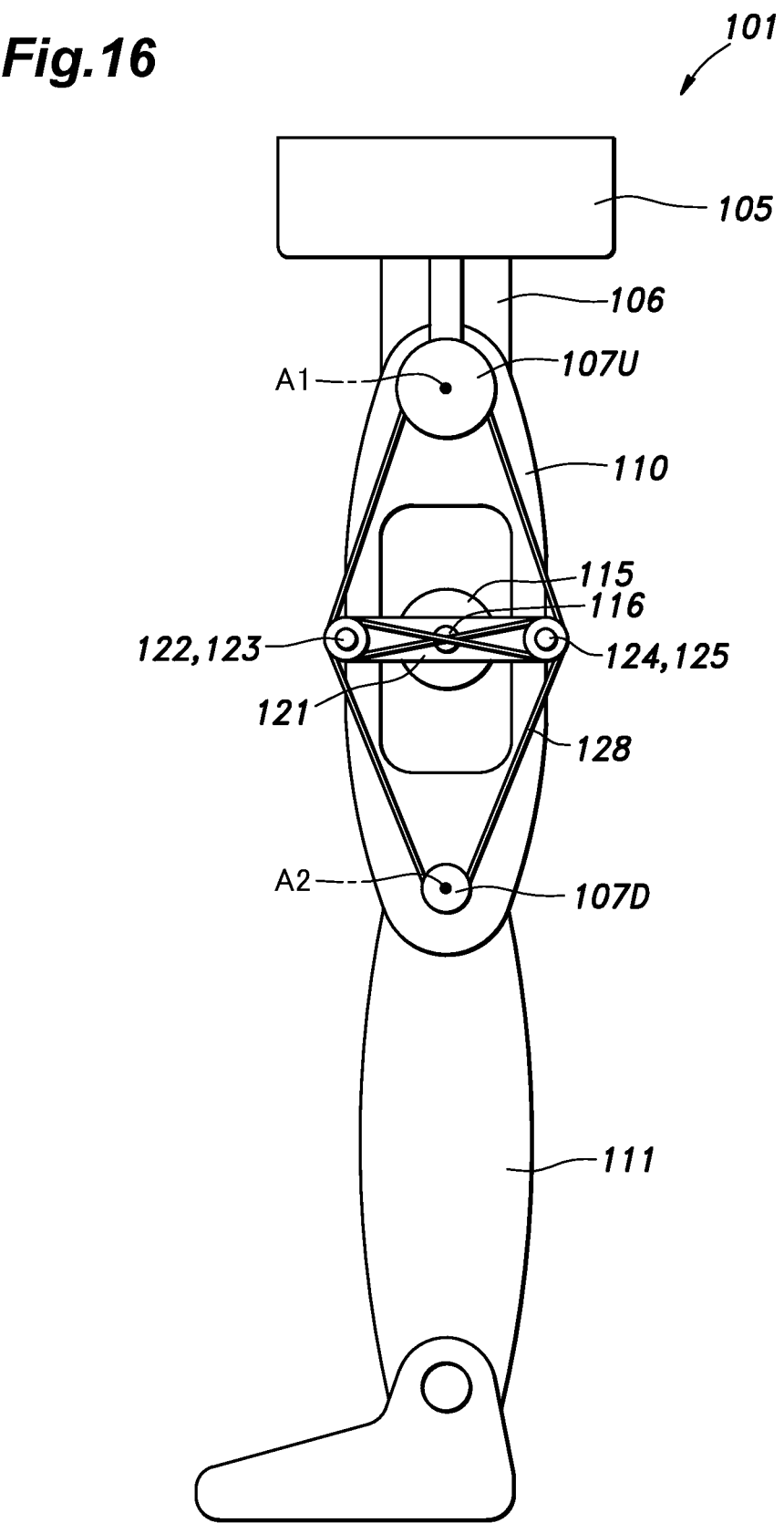
FIG. 16 is a view similar to FIG. 13 showing a modification of the second embodiment.
Figure 17:
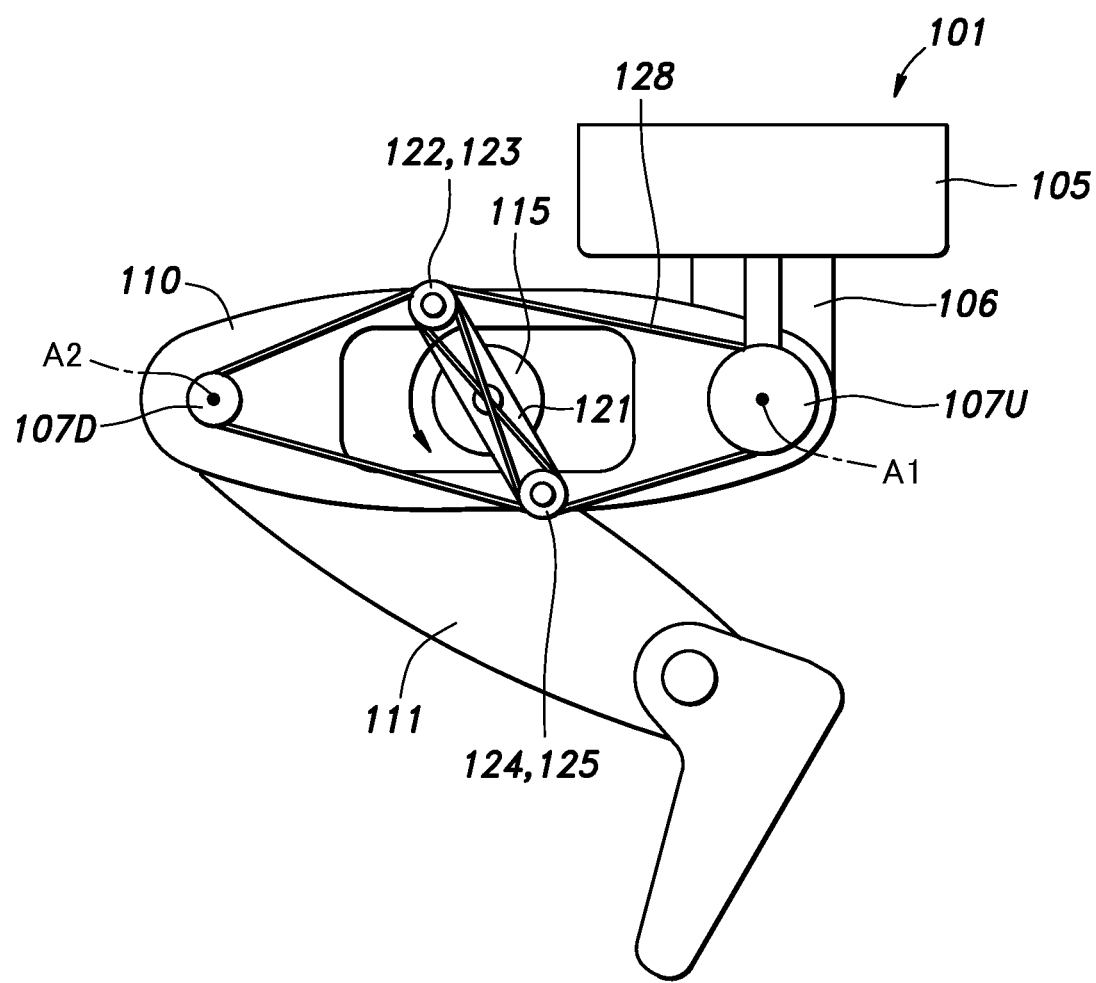
FIG. 17 is a view similar to FIG. 16 when the user is in a squatting posture with both the hip joint and the knee joint of the user flexed.

FIGS. 16 and 17 show a modification of the second embodiment which is similar to the second embodiment except for that the upper driven pulley 107U has a diameter twice as large as that of the lower driven pulley 107D.

According to this arrangement, when the upper leg member 110 rotates forward by a certain angle around the first axial line A1, the lower leg member 111 rotates rearward by twice this angle around the second axial line A2 relative to the upper leg member 110 as shown in FIG. 17. Therefore, the rotational angle of the lower leg member 111 is substantially equal to that of the upper leg member 110 in absolute space. When the rotation of the rotary arm 121 is reversed, the upper leg member 110 and the lower leg member 111 are moved to return to their respective original upright attitude to assist rising of the user U from the squatting posture.

Therefore, according to this arrangement, the rising assist device 101 is able to assist the user U to rise upright from the squatting posture. In this embodiment also, the user U is allowed to sit or otherwise flex the hip joint and the knee joint independently from each other.

Although the present invention has been described in terms of preferred embodiments thereof, it is obvious to a person skilled in the art that various alterations and modifications are possible without departing from the scope of the present invention. For instance, the body part to be assisted is not limited to those discussed in the foregoing embodiments, but may consist of upper and/or lower arm of the user. Also, the drive source may consist of other drive sources such as pneumatic and hydraulic motors. The term drive belt as used in the claims of this application should be interpreted in the broadest sense, and may be selected from belts, chain links, cables or other flexible power transmission members. Depending on the particular form of the drive belt, the pulley may take various forms such as pulleys, sprockets, rollers or other rotating bodies for transmitting power to the belt.

The invention claimed is:

1. A motion assist device for assisting a motion of a body part of a user, comprising:
    a support member extending in a prescribed direction, and configured to be worn by a first body part of the user;
    a first link member connected to a first end of the support member so as to be rotatable around a first axial line and configured to be worn by a second body part of the user;
    a second link member connected to a second end of the support member so as to be rotatable around a second axial line and configured to be worn by a third body part of the user;
    a drive source mounted on the support member; and
    a power transmission mechanism for transmitting a power of the drive source to the first link member and the second link member;
    wherein the power transmission mechanism includes:
    a rotary arm rotatably supported by the support member at an intermediate point of the rotary arm and driven to rotate by the drive source;
    a first drive pulley and a second drive pulley supported by one end of the rotary arm so as to be rotatable around a common axial line or mutually parallel axial lines;
    a third drive pulley and a fourth drive pulley supported by another end of the rotary arm so as to be rotatable around a common axial line or mutually parallel axial lines;
    a first driven pulley fixedly secured to the first link member in a coaxial relationship to the first axial line;
    a second driven pulley fixedly secured to the second link member in a coaxial relationship to the second axial line;
    a first drive belt passed around the first driven pulley, the first drive pulley, the third drive pulley and the second driven pulley in that order; and
    a second drive belt passed around the second driven pulley, the second drive pulley, the fourth drive pulley and the first driven pulley in that order;
    wherein the first drive belt is passed around the first drive pulley and the third drive pulley in a cross belt drive, and the second drive belt is passed around the second drive pulley and the fourth drive pulley in the cross belt drive.

2. The motion assist device according to claim 1, wherein the rotary arm is positioned centrally between the first and second drive pulleys, and is provided with a neutral position where a lengthwise direction of the rotary arm is substantially orthogonal to a line connecting the first and second drive pulleys to each other.

3. The motion assist device according to claim 1, wherein the first drive belt and the second drive belt are passed around both the first driven pulley and the second driven pulley in an open belt drive.

4. The motion assist device according to claim 1, wherein the first drive belt and the second drive belt are passed around the first driven pulley in a cross belt drive and the second driven pulley in an open belt drive.

5. The motion assist device according to claim 1, further comprising idler pulleys for preventing a slacking of the first drive belt and the second drive belt.

6. The motion assist device according to claim 5, wherein the rotary arm is positioned centrally between the first and second drive pulleys, and is provided with a neutral position where a lengthwise direction of the rotary arm is substantially orthogonal to a line connecting the first and second drive pulleys to each other,
    and wherein the idler pulleys include a pair of idler pulleys located on either lateral side of the one end of the rotary arm in the neutral position and another pair of idler pulleys located on either lateral side of the other end of the rotary arm in the neutral position, such that the idler pulleys push the drive belts outward.

7. The motion assist device according to claim 1, wherein the first drive belt and the second drive belt consist of a single endless drive belt.

8. The motion assist device according to claim 1, wherein the first body part is a pelvic part of the user, and the second and third body parts are right and left upper legs of the user.

9. The motion assist device according to claim 1, wherein the first body part is an upper leg of the user, the second body part is a pelvic part of the user, and the third body part is a lower leg of the user.

10. The motion assist device according to claim 1, wherein the first driven pulley and the second driven pulley have a same diameter.

11. The motion assist device according to claim 1, wherein the first driven pulley and the second driven pulley have different diameters.

* * * * *